United States Patent
Kumar (10) Patent No.: US 12,043,881 B2
(45) Date of Patent: Jul. 23, 2024

(54) WIRES OF SUPERELASTIC NICKEL-TITANIUM ALLOY AND METHODS OF FORMING THE SAME

(71) Applicant: W. L. Gore & Associates, Inc., Newark, DE (US)

(72) Inventor: Parikshith K. Kumar, Flagstaff, AZ (US)

(73) Assignee: W. L. Gore & Associates, Inc., Newark, DE (US)

(*) Notice: Subject to any disclaimer, the term of this patent is extended or adjusted under 35 U.S.C. 154(b) by 14 days.

(21) Appl. No.: 17/764,461

(22) PCT Filed: Sep. 25, 2020

(86) PCT No.: PCT/US2020/052778
§ 371 (c)(1),
(2) Date: Mar. 28, 2022

(87) PCT Pub. No.: WO2021/062191
PCT Pub. Date: Apr. 1, 2021

(65) Prior Publication Data
US 2022/0349030 A1  Nov. 3, 2022

Related U.S. Application Data

(60) Provisional application No. 62/907,500, filed on Sep. 27, 2019.

(51) Int. Cl.
*C22C 19/00* (2006.01)
*C22F 1/00* (2006.01)
*C22F 1/10* (2006.01)
*C22F 1/18* (2006.01)

(52) U.S. Cl.
CPC ............ *C22C 19/007* (2013.01); *C22F 1/006* (2013.01); *C22F 1/10* (2013.01); *C22F 1/183* (2013.01)

(58) Field of Classification Search
CPC ............ C22F 1/183; C22F 1/10; C22F 1/006; C22C 19/007
See application file for complete search history.

(56) References Cited

U.S. PATENT DOCUMENTS

| | | | |
|---|---|---|---|
| 4,707,196 A | 11/1987 | Honma et al. |
| 5,411,476 A | 5/1995 | Abrams et al. |
| 5,882,444 A | 3/1999 | Flomenblit et al. |
| 6,217,567 B1 | 4/2001 | Zadno-Azizi et al. |
| 7,455,738 B2 | 11/2008 | Patel et al. |
| 7,789,979 B2 | 9/2010 | Dooley et al. |
| 8,118,952 B2 | 2/2012 | Gall et al. |
| 8,414,714 B2 | 4/2013 | Schaffer |
| 8,888,838 B2 | 11/2014 | Blanzy |
| 9,169,545 B2 | 10/2015 | Padula, II et al. |
| 9,422,615 B2 | 8/2016 | Greene et al. |
| 9,878,366 B2 | 1/2018 | Johnson |
| 9,976,297 B2 | 5/2018 | Danning |
| 2007/0293939 A1 | 12/2007 | Shrivastava et al. |
| 2010/0075168 A1 | 3/2010 | Schaffer |
| 2012/0282571 A1 | 11/2012 | Ammon et al. |
| 2014/0242543 A1 | 8/2014 | Johnson |
| 2018/0153718 A1 | 6/2018 | Armstrong et al. |
| 2020/0209068 A1 | 7/2020 | Kise et al. |
| 2022/0290275 A1 | 9/2022 | Born et al. |

FOREIGN PATENT DOCUMENTS

| | | |
|---|---|---|
| CN | 107080598 A | 8/2017 |
| CN | 110431246 A | 11/2019 |
| JP | 09-078165 A | 3/1997 |
| WO | 2010/051515 A1 | 5/2010 |
| WO | 2014/078670 A1 | 5/2014 |
| WO | 2016/012236 A1 | 1/2016 |
| WO | 2016/077777 A1 | 5/2016 |

OTHER PUBLICATIONS

Laplanche, G., et al. "Effect of temperature and texture on the reorientation of martensite variants in NiTi shape memory alloys." Acta Materialia 127 (2017): 143-152.*
Kajzer, W., et al. "Surface modification and corrosion resistance of Ni—Ti alloy used for urological stents." Journal of Achievements in Materials and Manufacturing Engineering 20.1-2 (2007): 123-126.*
International Preliminary Report on Patentability received for PCT Patent Application No. PCT/US2020/052766, mailed on Feb. 2, 2022, 17 pages.
International Preliminary Report on Patentability received for PCT Patent Application No. PCT/US2020/052778, mailed on Feb. 2, 2022, 14 pages.
International Search Report and Written Opinion received for PCT Patent Application No. PCT/US2020/052766, mailed on Nov. 9, 2020, 12 pages.
International Search Report and Written Opinion received for PCT Patent Application No. PCT/US2020/052778, mailed on Nov. 12, 2020, 13 pages.
Khalil H. F. et al., "Changes in the Mechanical Behavior of Nitinol Following Variations of Heat Treatment Duration and Temperature," Georgia Institute of Technology, Dec. 2009, 59 pages.
Kim et al., "Ageing-induced two-stage R-phase transformation in Ti-50.9at.%Ni," Acta Materialia, vol. 52, 2004) 487-499.
Wang et al., "Effect of grain size on aging microstructure as reflected in the transformation behavior of a low-temperature aged Ti-50.8 at.% Ni alloy," Scripta Materialia, vol. 69, Jul. 1, 2013, pp. 545-548.
Zhou et al., "Origin of 2-stage R-phase transformation in low-temperature aged Ni-rich Ti—Ni alloys," Acta Materialia, vol. 53, Sep. 28, 2005, pp. 5365-5377.
Zhou et al., "Understanding of multi-stage R-phase transformation in aged Ni-rich Ti—Ni shape memory alloys," Materials Science and Engineering A, vol. 438-440, Nov. 25, 2006, pp. 602-607.

* cited by examiner

Primary Examiner — Jessee R Roe (57) ABSTRACT

A nickel-titanium alloy with an average grain size of between 0.2 and 10 microns and a recoverable strain of greater than 9% is disclosed herein, in which the alloy is formed using a method which involves applying a shape set heat treatment to the nickel-titanium alloy. The heat treatment includes applying heat at a temperature between 225° C. and 350° C. for a period of time between 20 and 240 minutes.

15 Claims, 5 Drawing Sheets

WIRES OF SUPERELASTIC NICKEL-TITANIUM ALLOY AND METHODS OF FORMING THE SAME

CROSS-REFERENCE TO RELATED APPLICATION

The present application is a national phase application of PCT Application No. PCT/US2020/052778, internationally filed on Sep. 25, 2020, which claims priority to U.S. Provisional Application No. 62/907,500 filed Sep. 27, 2019, the disclosure of which are incorporated herein by reference in their entireties.

FIELD

The invention relates generally to nickel-titanium alloys and methods of manufacturing the same.

BACKGROUND

There has been great interest in shape memory and superelastic alloys such as nickel-titanium. This family of alloys is also known as nitinol (i.e., Nickel-Titanium Naval Ordinance Laboratory). Key to exploiting the performance of nitinol alloys is the phase transformation in the crystalline structure that transitions between an austenitic phase and a martensitic phase. The austenitic phase is commonly referred to as the high temperature phase, and the martensitic phase is commonly referred to as the low temperature phase. The specific phase properties, and the repeatable change from one phase to the other is the mechanism for achieving unique superelasticity and shape memory properties of nitinol.

Nickel-titanium alloys are frequently used in medical devices for diagnosis and treatment. Minimally invasive implantation of medical devices, for example, may require a device that may be retracted to a smaller size for delivery to a target treatment site, and then released and expanded to a functional configuration, exploiting the superelastic and/or shape memory properties of nitinol. There is a need for enhancement in nitinol material properties and manufacturing process to produce nickel-titanium alloys with properties such as superelasticity increased to beyond the currently known 6% superelasticity, particularly suitable in medical devices where smaller retracted profile is preferred while maintaining or improving the properties of the nickel-titanium alloys.

SUMMARY

Various disclosed concepts relate to a nickel-titanium alloy. According to one example ("Example 1"), the alloy has an average grain size between 0.2 and 10 microns and a recoverable strain of greater than 9%.

According to another example ("Example 2") further to Example 1, the nickel-titanium alloy has an upper plateau length of greater than 7%.

According to another example ("Example 3") further to Example 1 or 2, the nickel-titanium alloy has a lower plateau stress of less than 250 MPa.

According to another example ("Example 4") further to any preceding Example, the nickel-titanium alloy has an upper plateau stress of less than 400 MPa.

According to another example ("Example 5") further to any preceding Example, the nickel-titanium alloy has an elongation at fracture of greater than 15%.

According to another example ("Example 6") further to any preceding Example, the alloy is formed into an implantable medical device.

According to another example ("Example 7"), a nickel-titanium alloy formed using a method which includes providing the nickel-titanium alloy with an average grain size between 0.2 and 10 microns and applying a shape set heat treatment to the nickel-titanium alloy. The heat treatment includes applying heat at a temperature between 225° C. and 350° C. for a period of time between 20 and 240 minutes.

According to another example ("Example 8") further to Example 7, the nickel-titanium alloy has a recoverable strain of greater than 9%.

According to another example ("Example 9") further to Example 7 or 8, the nickel-titanium alloy has an upper plateau length of greater than 6%.

According to another example ("Example 10") further to any one of Examples 7 to 9, the nickel-titanium alloy has a lower plateau stress of less than 250 MPa.

According to another example ("Example 11") further to any one of Examples 7 to 10, the nickel-titanium alloy has an upper plateau stress of less than 400 MPa.

According to another example ("Example 12") further to any one of Examples 7 to 11, the nickel-titanium alloy has an elongation at fracture of greater than 15%.

According to another example ("Example 13") further to any one of Examples 7 to 12, the alloy is formed into an implantable medical device.

According to another example ("Example 14"), a method is disclosed for forming a nickel-titanium alloy. The method includes providing the nickel-titanium alloy in a cold worked state of between 35% and 46%, applying a partial annealing heat treatment at a temperature between 550° C. and 700° C. for a period of time up to 60 minutes, and applying a heat treatment to the nickel-titanium alloy. The heat treatment includes applying heat at a temperature between 225° C. and 350° C. for a period of time between 20 and 240 minutes.

According to another example ("Example 15") further to Example 14, the nickel-titanium alloy has a recoverable strain of greater than 9%.

According to another example ("Example 16") further to Example 14 or 15, the nickel-titanium alloy has an upper plateau length of greater than 6%.

According to another example ("Example 17") further to any one of Examples 14 to 16, the nickel-titanium alloy has a lower plateau stress of less than 250 MPa.

According to another example ("Example 18") further to any one of Examples 14 to 17, the nickel-titanium alloy has an upper plateau stress of less than 400 MPa.

According to another example ("Example 19") further to any one of Examples 14 to 18, the nickel-titanium alloy has an elongation at fracture of greater than 15%.

According to another example ("Example 20") further to any one of Examples 14 to 19, the method further includes forming the nickel-titanium alloy into an implantable medical device.

The foregoing examples are just that, and should not be read to limit or otherwise narrow the scope of any of the inventive concepts otherwise provided by the instant disclosure. While multiple examples are disclosed, still other embodiments will become apparent to those skilled in the art from the following detailed description, which shows and describes illustrative examples. Accordingly, the drawings and detailed description are to be regarded as illustrative in nature rather than restrictive in nature.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

DETAILED DESCRIPTION

Definitions and Terminology

This disclosure is not meant to be read in a restrictive manner. For example, the terminology used in the application should be read broadly in the context of the meaning those in the field would attribute such terminology.

With respect to terminology of inexactitude, the terms "about" and "approximately" may be used, interchangeably, to refer to a measurement that includes the stated measurement and that also includes any measurements that are reasonably close to the stated measurement. Measurements that are reasonably close to the stated measurement deviate from the stated measurement by a reasonably small amount as understood and readily ascertained by individuals having ordinary skill in the relevant arts. Such deviations may be attributable to measurement error or minor adjustments made to optimize performance, for example.

The term "Nitinol" (NiTi) refers to a near-equiatomic alloy of nickel and titanium (which may contain ternary, quaternary, or more elements such as copper, chromium, iron, vanadium, cobalt, or niobium, etc.). "Nitinol alloy(s)", "NiTi alloy(s)", "nickel-titanium alloy(s)", and/or "NiTi alloy material(s)" may be used interchangeably throughout the disclosure to refer to NiTi exhibiting shape-memory or superelastic behavior Furthermore, although the term "wire" is mentioned in some examples throughout the disclosure, it is to be appreciated that other forms of metal such as sheet and stent frames, etc., may experience the same processes as the wire to achieve same or similar mechanical properties as disclosed herein.

The term "cold working" refers to a process in which a metal material is shaped below its recrystallization temperature, for example at an ambient temperature. During a cold drawing process of cold working, a wire is pulled through a lubricated die to reduce its diameter. The deformation associated with the wire drawing increases the stress in the material, and the stress eventually must be relieved by various methods of heat treatment or annealing at elevated temperatures to restore ductility, thus enabling the material to be further cold worked to a smaller diameter. The cold work is typically expressed in terms of a percentage that represents the reduction in the cross sectional area during the final pass through the die. Initial preparation of a wire may begin with a rod stock, followed by one or more iterations of cold working and annealing. The physical properties of the wire are determined based on the cold working process and the annealing process. Cold working includes squeezing, bending, drawing, and shearing being performed on the wire to cause work hardening on the portions of the wire to undergo plastic deformation to achieve a shape change. Cold working is called as such because the procedure is performed at a temperature below a recrystallization temperature of the alloy from which the wire is made.

The term "annealing" or "annealing heat treatment" includes either a full annealing heat treatment or a partial annealing heat treatment. A full annealing heat treatment can result in a material with a random crystal orientation, and the various material or fiber "textures" that are generated during cold wire drawing are mostly eliminated during a full annealing and recrystallization. During a partial annealing process, grain growth and recrystallization occurs but a certain amount of the material texture generated during cold wire drawing process is retained. The partial annealing may also be referred to as a cold work-reducing annealing process.

Description of Various Embodiments

Figure 1:
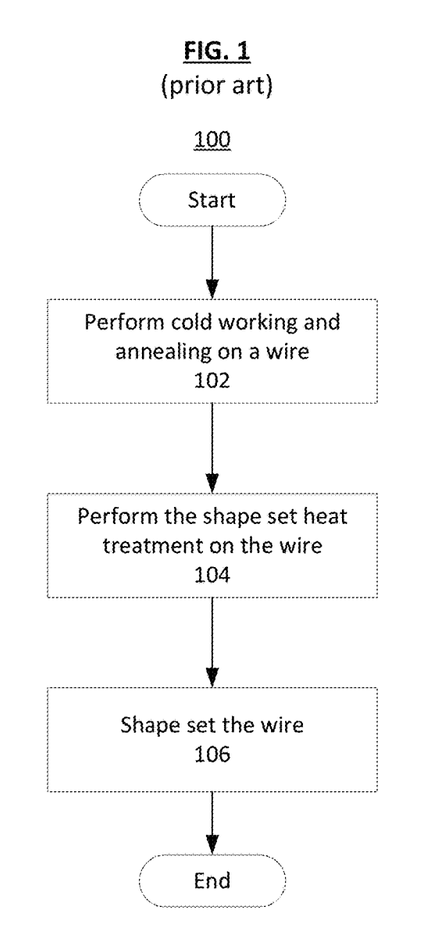
FIG. 1 shows a flow diagram of the different steps associated with the processing (cold working, annealing and shape setting) of a NiTi (nickel-titanium) alloy through conventional processing methods.

FIG. 1 shows a conventional treatment process 100 that causes a product, such as a wire, made of nickel-titanium alloy to gain its properties. Wire products made of shape memory materials are manufactured by forming a relatively thick piece of hot-worked rod stock from a melt process. The rod stock is then further processed into wires by drawing the rod stock down to a thin diameter wire using a combination of cold working and annealing.

Conventional wire annealing typically results in grain growth. Typical annealing temperatures for nitinol is greater than 550° C. for a range of different times.

In the step 102 of the process 100, the wire undergoes the aforementioned cold working and annealing process. Cold working includes squeezing, bending, drawing, and shearing, among other actions, being performed on the wire to cause desirable work hardening on the portions of the wire to undergo plastic deformation, thus achieving a shape change. Cold working is called as such because the procedure is performed at a temperature below a recrystallization temperature of the alloy that the wire is made of. The dislocations formed during the cold working pile up leading to internal stress fields within the wire, thereby producing closed loop superelasticity. However, if there are too much cold working performed on the wire, the wire may suffer a reduction in the material participating in the transformation, such that much of the material forming the wire are pinned or locked within it. The intermediate annealing heat treatment helps restore the ductility to the wire and alternate use of cold working and annealing helps reduce the bar stock to the desired wire size. In some examples, the step 102 causes the wire to be in a cold worked state of between 35% and 46%.

In step 104, the wire then goes through a subsequent heat treatment step or process often termed as "shape setting" or "shape setting heat treatment". This step forms the nitinol wire (or in some examples, tube or sheet) into a specific geometry by constraining the material into its new shape by fixing it to a mandrel prior to the shape set heat treatment. Additional shape setting step 106 follows the heat treatment of the step 104 if the desired resulting shape includes a complex geometry. For nitinol and its alloys typical shape setting temperatures can range from 400° C. to 550° C. for shape set heat treatment times up to 40 minutes.

Figure 2:
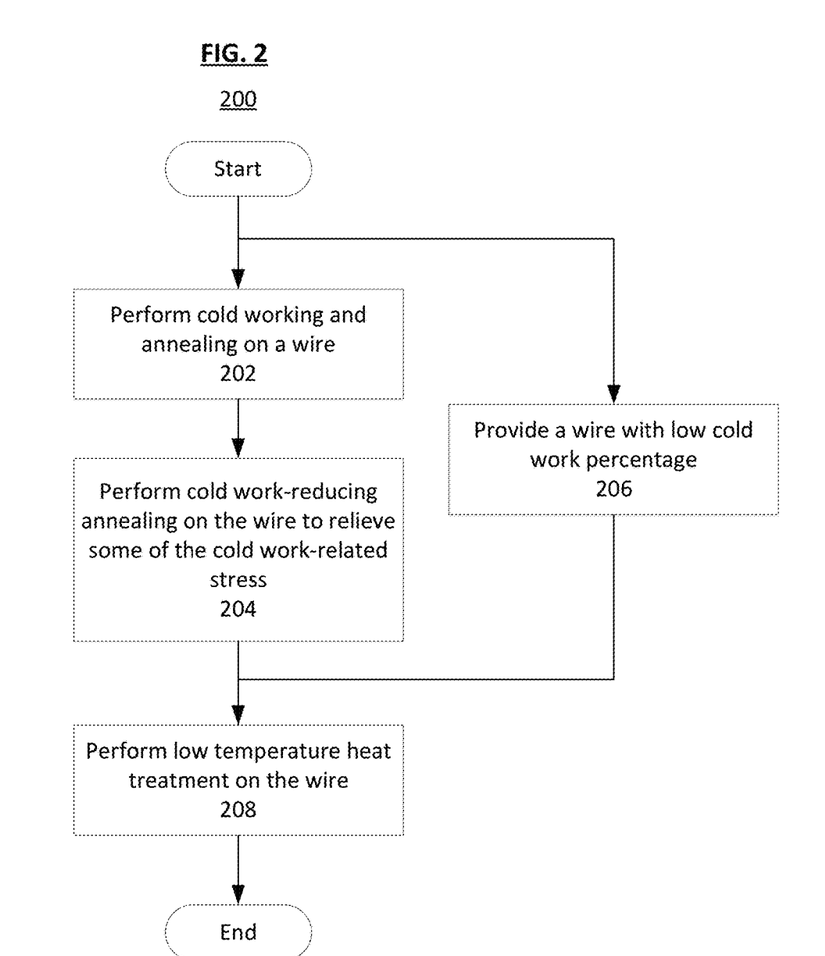
FIG. 2 shows a flow diagram of the steps associated with the method to process (cold work, annealing and shape setting) a NiTi (nickel-titanium) alloy according to an embodiment disclosed herein.

FIG. 2 shows a treatment process 200 as disclosed herein. The step 202 of the process 200 has the wire undergoing the aforementioned cold working and annealing process explained in the step 102. Cold working includes squeezing, bending, drawing, and shearing, among other actions, being performed on the wire to cause desirable work hardening on the portions of the wire to undergo plastic deformation, thus achieving a shape change. Cold working is performed at a temperature below a recrystallization temperature of the alloy. The dislocations formed during the cold working pile up leading to internal stress fields within the wire, thereby producing closed loop superelasticity. However, if there is too much cold working performed on the wire, the wire may suffer a reduction in the material participating in the transformation, such that much of the material forming the wire are pinned or locked within it. The intermediate annealing heat treatment helps restore the ductility to the wire and alternate use of cold working and annealing helps reduce the bar stock to the desired wire size. In some examples, the step 202 causes the wire to be in a cold worked state of between 35% and 40%, 40% and 42%, 42% and 44%, 44% and 46%, or any combination thereof.

In step 204, the wire undergoes a cold work-reducing annealing process in which the wire is heated to a temperature, for example via fluidized bath, salt pot or air furnace, that is above the recrystallization temperature of the alloy and below the melting temperature, maintaining the wire in the temperature for an amount of time, and then cooling the wire, in order to partially relieve the stress incurred on the wire by the cold working process, i.e. reducing the cold work. In some examples, the temperature of the cold work-reducing annealing process is between 550° C. and 700° C. In some examples, the temperature ranges from 550° C. to 600° C., 600° C. to 650° C., 650° C. to 700° C., or any combination thereof. In some examples, the cold work-reducing annealing process lasts for a period of time of up to 30 minutes, up to 45 minutes, or up to 60 minutes, for example. In some examples, the amount of cold work that is reduced by the cold work-reducing annealing process of the step 204 is greater than 5%, greater than 7%, greater than 10%, greater than 12%, greater than 15%, greater than 20%, or any value therebetween.

The cold work-reducing annealing process from the step 204 can result in the annihilation of dislocations and thereby reducing the internal stresses that enable closed loop superelasticity. On the other hand, precipitation formed by performing subsequent heat treatment on the wire enables coherent stress fields within the wire, but the formation of precipitation alone cannot produce closed loop superelasticity. As such, sufficient cold working process is necessary to be combined with the precipitation to cause closed loop superelasticity. The step 204 can be done following the step 202 such that the wire is received in a form with substantially lesser cold work.

Alternately, the wire can be processed to have lesser cold work (i.e. lesser reduction in cross section area in the last step) as shown by step 206, in which a wire is provided such that the wire has a low cold work percentage. In some examples, the low cold work percentage is defined as below 35%, below 30%, below 25%, below 20%, or any range therebetween. In some examples, the wire after the step 204 and the wire provided in the step 206 both have an average grain size ranging from 0.2 to 0.5 micron, 0.5 to 1 micron, 1 to 2 microns, 2 to 4 microns, 4 to 6 microns, 6 to 8 microns, 8 to 10 microns, or any combination thereof.

The wire then undergoes a low temperature heat treatment process, as per step 208, where the temperature of the heat treatment process is lower than the conventional shape set heat treatment temperature as explained in the step 104. For example, the shape setting heat treatment process of step 104 is in a temperature range of between 400° C. and 530° C., while a temperature of the low temperature shape set heat treatment process of step 208 ranges between 225° C. and 350° C. In some examples, the heat treatment temperature ranges between 225° C. and 270° C., 270° C. and 300° C., 300° C. and 320° C., 320° C. and 350° C., or any combination thereof.

The time in which each process takes place also varies. In some examples, the shape set heat treatment process of step 104 lasts between 5 and 40 minutes. In comparison, the low temperature shape set heat treatment process of step 208 in some examples takes longer, ranging from 20 minutes to 30 minutes, 30 minutes to 40 minutes, 40 minutes to 60 minutes, 60 minutes to 120 minutes, 120 minutes to 200 minutes, greater than 200 minutes, or any combination thereof. In some examples, the heat treatment process of step 208 lasts less than 60 minutes, while in other examples, the heat treatment process of step 208 lasts up to 240 minutes.

In some examples, the wire also undergoes a shape setting process during the heat treatment of step 208, which transforms the nitinol wire (or in some examples, tube or sheet) into a specific geometry by constraining the material into its new shape by fixing it to a mandrel prior to the heat treatment. In some examples, additional shape setting process(es) similar to the previously mentioned step 106 (not shown in FIG. 2) follows the heat treatment of step 208 if the desired resulting shape includes a complex geometry.

Figure 3:
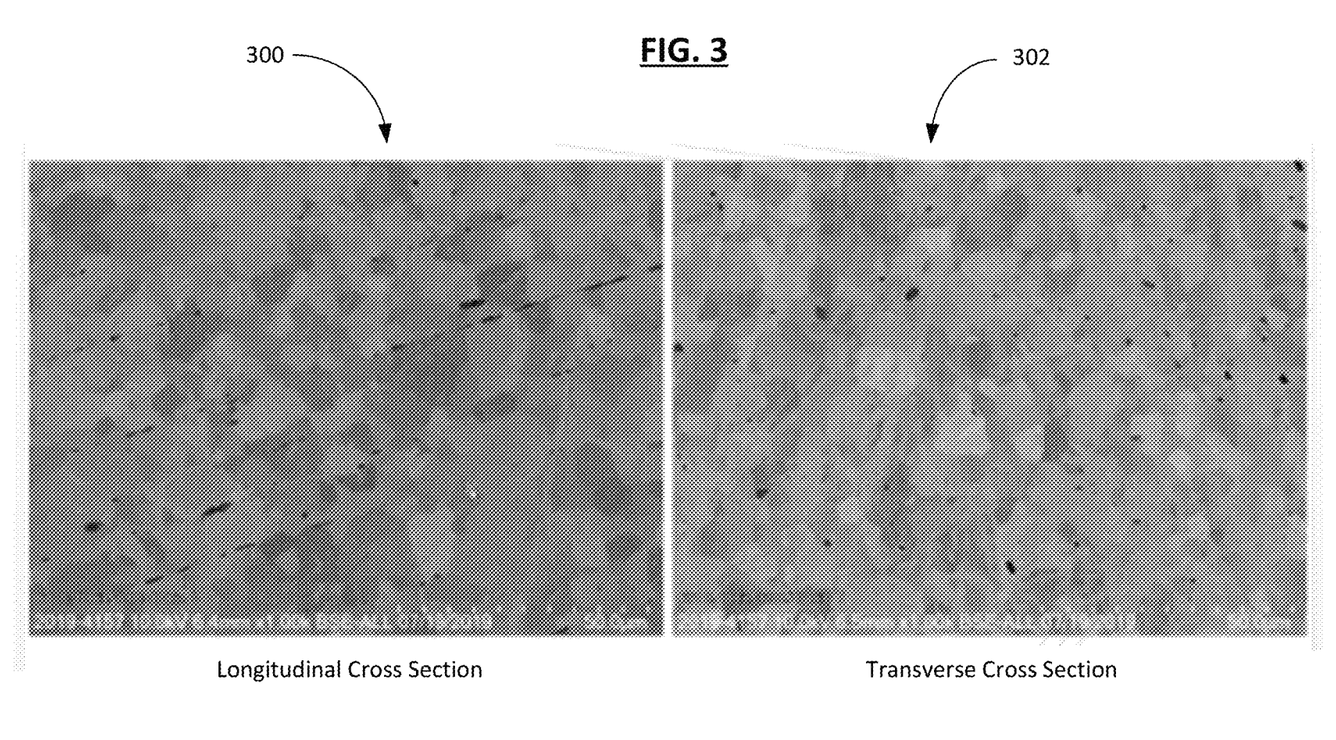
FIG. 3 shows an example of a cross-sectional microstructure of the wire as formed using a method disclosed herein.

FIG. 3 shows a close-up view of a cross-sectional surface of the wire that is treated using the process 200 explained above. For example, an image 300 is the view of the wire as cut longitudinally with respect to the length of the wire, and an image 302 is the view of the wire as cut transversely with respect to the length of the wire. In some examples, the wire shown in the image 300 or 302 indicates an average size grain size of 0.2 to 10 microns and an austenitic finish transformation temperature of −100° C. to 50° C. In some examples, the grain size increases when the temperature of the annealing heat treatment process increases.

During each of the aforementioned steps in the process 200, the physical properties of the wire undergo changes, where the physical properties include modulus, permanent set, recoverable strain, plateau stresses, as well as other properties as discussed further herein. These properties are measured using a testing method known as ASTM F2516 Standard Test Method for Tension Testing of Nickel-Titanium Superelastic Materials. In the ASTM F2516 method, a sample of nitinol wire is loaded by securing the two ends of the wire in fixtures of a measuring apparatus. After the wire is securely fixed to the measuring apparatus, the two ends of the wire are pulled farther away from each other at a specified rate until the wire reaches a specified strain percentage. In some examples, this specified strain percentage is 6% of the length of the wire. Then, the direction of the movement of the two ends of the wire is reversed such that the two ends are brought closer to each other until the load reaches below a predetermined limit. Lastly, the two ends of the wire are pulled apart again, this time until the wire breaks. The measurements taken at each step are used to make a stress-strain curve that represents the physical properties of the nitinol being tested. An example of such stress-strain curve is shown in FIG. 4, as explained below.

Figure 4:
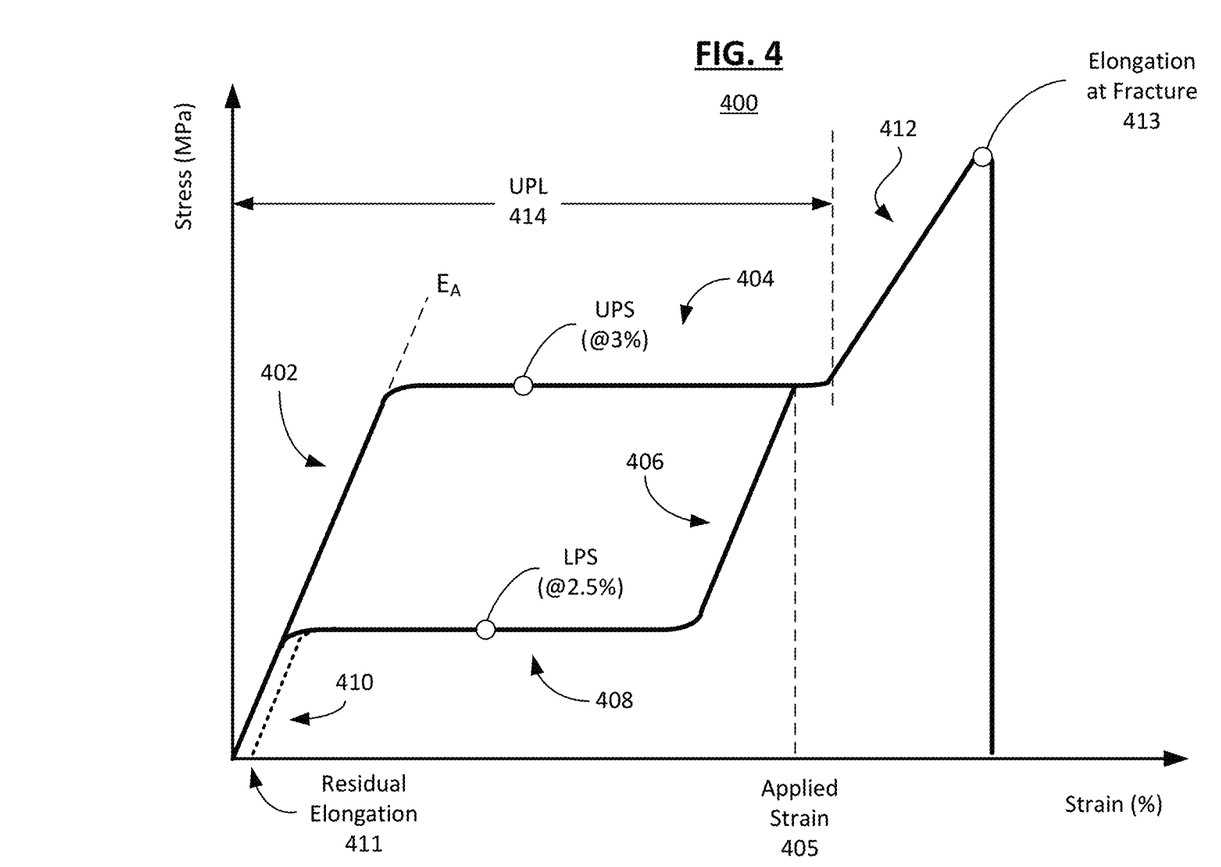
FIG. 4 shows an example of a stress-strain curve of a wire formed in an embodiment according to the method disclosed herein.

FIG. 4 shows an example of a stress-strain curve 400 showing the closed loop superelasticity of the nitinol wire. The stress-strain curve 400 includes some of the characteristics of the nitinol wire that can be determined using the ASTM F2516 method. When the initial strain is applied to the wire by pulling the two ends in opposite directions, the wire undergoes linear elastic (non-permanent) deformation 402 with a slope of $E_A$ (i.e. Young's modulus or elastic modulus) defining the ratio of tensile stress to tensile strain. Then, the tensile stress experiences a flat region or plateau 404 in which the wire undergoes tensile strain without additional stress applied to it. According to the specification of the ASTM F2516 method, an upper plateau stress (UPS) is defined as the stress measured in this plateau 404, more particularly at 3% strain when the tensile stress is initially applied. Then, according to the specification of the ASTM F2516 method, the tensile stress is applied until the strain reaches an applied strain 405, which according to the ASTM F2516 specification is 6%, which is the initial load strain or a recoverable (i.e., reversible) strain for testing nitinol, after which the direction is reversed during an unloading process 406 which brings the two ends of the wire closer together. The wire undergoes another plateau 408 in this process, and a lower plateau stress (LPS) is measured, according to the specification of the ASTM F2516 method, at 2.5% strain after the wire reaches the initial 6% strain. The difference between the values for the UPS 404 and LPS 408 is called mechanical hysteresis. It should be noted that for different values of the applied strain 405, different amounts of residual elongation 411 are observed. The recoverable strain is the strain at which little or no residual elongation 411 is observed (e.g., less than 0.5%) after the strain 405 is applied.

Thereafter, the wire has 7 MPa of stress being applied thereto, according to the specification of the ASTM F2516 method. In the absence of any other stress, the wire may return to the initial length. In many nitinol wires, the length of the wire does not change or change very little, for example less than 0.5% change in the length before and after the initial strain of 6% is reached, but in some cases, the resulting length of the wire is longer than the initial length. In these case, the wire is said to have undergone a permanent deformation 410 with a residual elongation 411 that is determined by comparing the resulting length of the wire with the initial length. Lastly, the two ends of the wire are pulled in opposite direction again such that the wire undergoes the elastic deformation 402 and the upper plateau 404. However, this time, the wire is pulled past the 6% strain and undergoes a second elastic loading region 412 which can be accompanied by plastic (permanent) deformation, after which the wire breaks, or fractures, thus representing the elongation at fracture 413 of the wire. In some examples, the elongation at fracture 413 is at 15% strain or greater. For any wire tested per the method listed above the upper plateau length (UPL) 414 is defined as the total strain from the start of the loading of the wire (i.e., at 0% strain) up to the end of the upper plateau 404 just before the second loading region 412. In some examples, the UPL 414 is greater than 7% strain, greater than 8% strain, or greater than 9% strain. In some examples, the UPS 404 is less than 400 MPa and the LPS 408 is less than 250 MPa.

Examples of methods that are used to process a nitinol wire are disclosed below as well as the resulting properties of each wire prepared using the process. Although these examples describe the use of nitinol wire, they can apply to other material forms such as tube or sheet. These methods are exemplary and not limiting; further uses will be recognized by a skilled artisan.

Example 1: A nitinol wire (for example: an ASTM F2516 complaint superelastic nitinol wire of 0.0206 inch or 0.523 mm wire diameter) shows an example of a typical NiTi wire heat treated between 450° C. and 500° C., for a time between 15 and 20 minutes. The heat treatment relieves some cold work and also causes precipitation to form in the wire that aids the process of precipitation hardening within the nitinol wire to increase the yield strength thereof.

Example 2: A nitinol wire undergoes a cold working process as mentioned in the step 202 of the process 200 shown above to reduce the diameter of the wire. Specifically, the nitinol wire undergoes the drawing process at room temperature (approximately 25° C.) which is well below the recrystallization temperature (550° C.) of the wire. Then, in the step 204, the wire undergoes an annealing process in which the wire is heated to a temperature that is above the recrystallization temperature (550° C.) of the alloy and below the melting temperature (1310° C.) and maintaining the wire in the temperature for an amount of time in order to partially relieve the cold work-related stress. In this example, the wire underwent an annealing process at 670° C. for 10 minutes. Thereafter, in the subsequent step 106, the partially annealed wire undergoes a low temperature heat treatment in which the wire is heated at a temperature below the recrystallization temperature, which in this example is 320° C., for 40 minutes.

Figure 5:
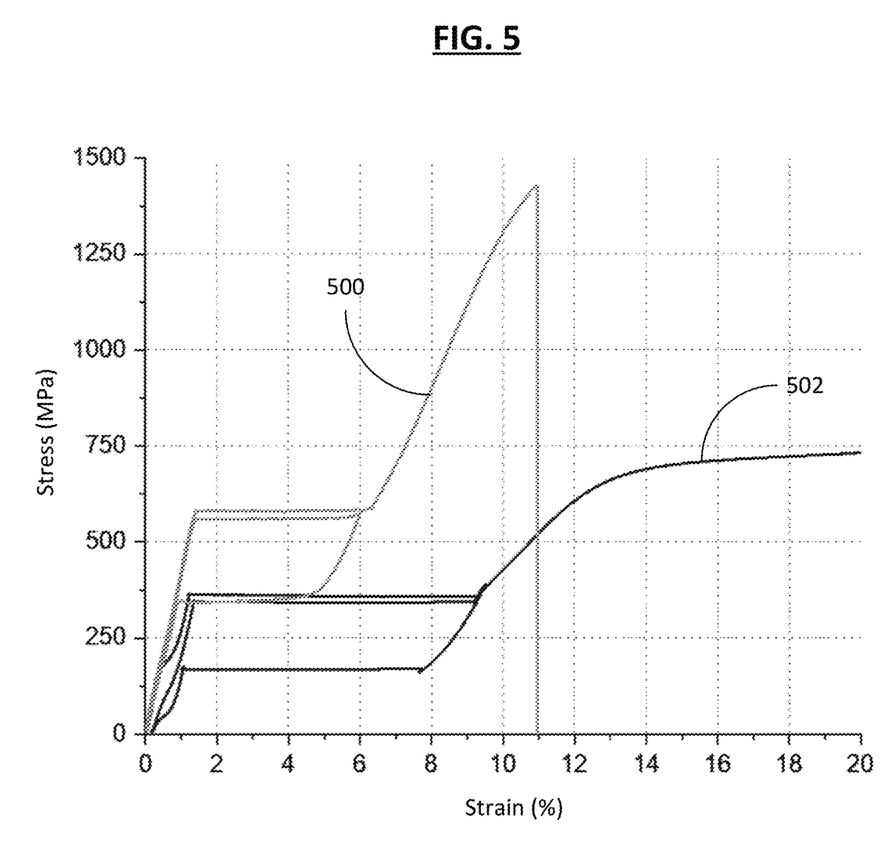
FIG. 5 shows an example of a stress-strain curve with different physical properties, formed using the processing method disclosed herein and compared to a typical stress-strain response obtained using conventional processing methods.

FIG. 5 compares the different closed-loop stress-strain curves 500 and 502 that result from processing the same NiTi alloy material according to Examples 1 and 2. Specifically, the stress-strain curve 500 is that of the processed wire in Example 1, and the stress-strain curve 502 is that of the processed wire in Example 2. As can be seen in FIG. 5, the curve 502 has a greater upper plateau length at 9.2%, whereas the curve 500 has a plateau length at 6%. Furthermore, the UPS 404 and the LPS 408 are also lower in the curve 502 than in the curve 500. Additionally, the elongation at fracture of the curve 500 is at 11% which is when the wire of Example 1 breaks under strain. On the other hand, the curve 502 can tolerate a higher strain than 11% without breaking, thereby showing the ductility of the wire of Example 2.

In some examples, the resulting wire has a recoverable strain of greater than 8%, greater than 9%, or greater than 10%. In some examples, the NiTi alloy is formed into a wire construct such as a wire-wound device. In some examples, the wire-wound device has a cover attached thereto to form a covered stent with a wire-wound NiTi tube. Other suitable constructs using the NiTi alloy are also envisioned, for example for medical purposes.

FIGS. 6A to 6D illustrate examples of various implantable medical devices which may be made using the wire as disclosed herein. The wire may be formed into any one or more of these medical devices using any suitable method known in the art. The examples are merely illustrative and are not meant to be exhaustive, and the shapes and configurations of the medical devices are not limited to those shown in the figures.

Figure 6A:
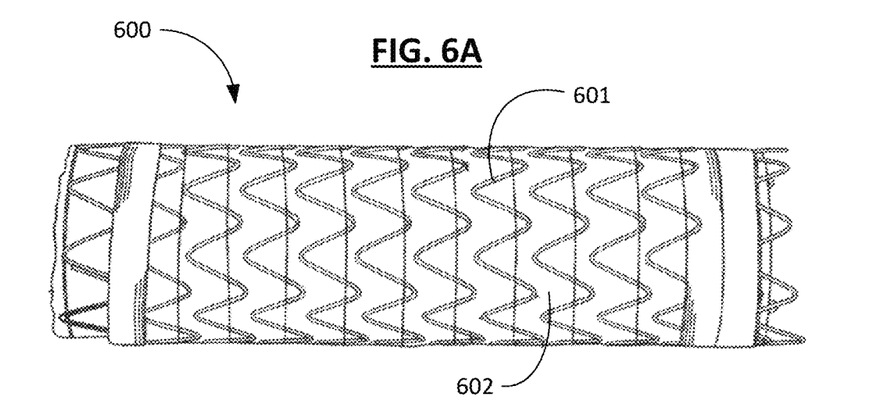
FIGS. 6A through 6D show examples of implantable medical devices which may be formed using the wire(s) as disclosed herein according to various embodiments.

FIG. 6A shows an example of a stent-graft 600 which includes one or more wire or stent 601 and one or more membranous material or graft 602. The wire or stent 601 may be helically formed surrounding the graft 602, although any suitable configuration may be envisioned.

Figure 6B:
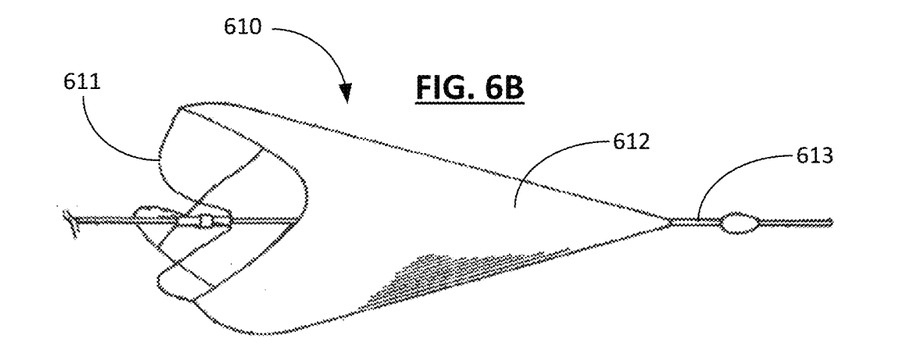

FIG. 6B shows an example of an embolic filter 610 which includes wires or struts 611 and one or more membranous material or filter element 612, which are affixed to a central support member 613. The struts 611 may be straight, curved, or have any other suitable shape and configuration.

Figure 6C:
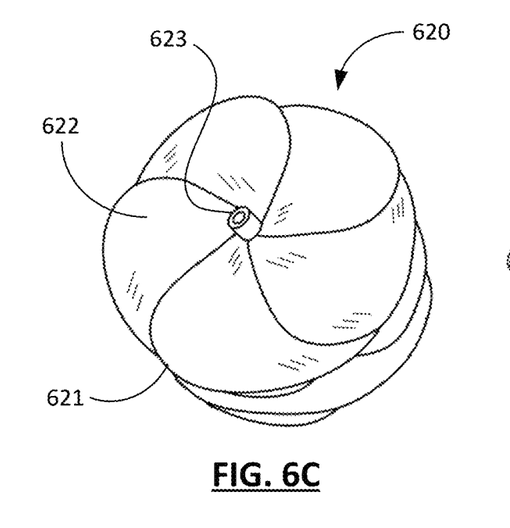

FIG. 6C shows an example of a septal occluder or cardiac sealing device 620 which includes one or more wire forming a wire frame 621, one or more membranous material or sealing member 622, and one or more eyelet 623 which may or may not be occluded to control fluid flow therethrough. The wire frame 621 may be attached to or implemented with the eyelet 623 and the sealing member 622 may be attached to the wire frame 621. The wire frame 621 may assume any suitable configuration as known in the art.

Figure 6D:
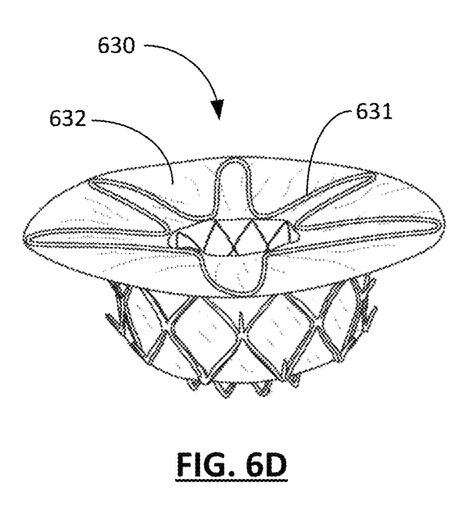

FIG. 6D shows an example of a heart valve or prosthetic retention element 630 which includes one or more wire forming a valve frame 631 and one or more membranous material or cover 632. The cover 632 may be attached to or implemented with the valve frame 631. The valve frame 631 may assume any suitable configuration as known in the art.

The embodiments and methods disclosed herein may be used to enable a variety of shape memory articles. The shape memory articles are preferably medical devices, more preferably implantable medical devices. The implantable medical devices are most preferably devices of nitinol shape memory alloy, most particularly that is superelastic at normal body temperature (approximately 37° C.). Implantable medical devices are defined as devices that are intended to remain within a living body for periods of 24 hours or longer.

The shape memory alloy articles may be produced from materials of various shapes, such as wire of various transverse cross sectional shapes including circular, elliptical, square, rectangular, etc. Alternatively, the articles may be made by machining precursor forms such as sheets, tubes or rods, as by electrical discharge machining (EDM), laser cutting, chemical milling, or the like.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A nickel-titanium alloy having an average grain size between 0.2 and 10 microns, a recoverable strain of greater than 9% in length, and an upper plateau stress (UPS) of less than 400 MPa, wherein the UPS is measured in response to applying the recoverable strain to the wire, and the nickel-titanium alloy undergoes a residual elongation of less than 0.5% in response to applying the recoverable strain.

2. The nickel-titanium alloy of claim 1, wherein the nickel-titanium alloy has an upper plateau length of greater than 7%.

3. The nickel-titanium alloy of claim 1, wherein the nickel-titanium alloy has a lower plateau stress (LPS) of less than 250 MPa, wherein the LPS is measured in response to applying the recoverable strain to the wire.

4. The nickel-titanium alloy of claim 1, wherein the nickel-titanium alloy has an elongation at fracture of greater than 15% in length.

5. The nickel-titanium alloy of claim 1, further formed into an implantable medical device.

6. A nickel-titanium alloy formed using a method comprising:
providing the nickel-titanium alloy with an average grain size between 0.2 and 10 microns; and
applying a shape set heat treatment to the nickel-titanium alloy to form the nickel-titanium alloy with a recoverable strain of greater than 9% in length and an upper plateau stress (UPS) of less than 400 MPa, wherein the UPS is measured in response to applying the recoverable strain to the wire, the heat treatment includes applying heat at a temperature between 225° C. and 350° C. for a period of time between 20 and 240 minutes, wherein the nickel-titanium alloy undergoes a residual elongation of less than 0.5% in response to applying the recoverable strain.

7. The nickel-titanium alloy of claim 6, wherein the nickel-titanium alloy has an upper plateau length of greater than 6%.

8. The nickel-titanium alloy of claim 6, wherein the nickel-titanium alloy has a lower plateau stress of less than 250 M Pa.

9. The nickel-titanium alloy of claim 6, wherein the nickel-titanium alloy has an elongation at fracture of greater than 15% in length.

10. The nickel-titanium alloy of claim 6, further formed into an implantable medical device.

11. A method of forming a nickel-titanium alloy, comprising:
providing the nickel-titanium alloy in a cold worked state of between 35% and 46%;
applying a partial annealing heat treatment of between 550° C. and 700° C. temperature for up to 60 minutes; and
applying a heat treatment to the nickel-titanium alloy to cause the nickel-titanium alloy to have a recoverable strain of greater than 9% in length and an upper plateau stress (UPS) of less than 400 M Pa, wherein the UPS is measured in response to applying the recoverable strain to the wire, the heat treatment includes applying heat of between 225° C. and 350° C. temperature for a period of time between 20 and 240 minutes.

12. The method of claim 11, wherein the nickel-titanium alloy has an upper plateau length of greater than 6%.

13. The method of claim 11, wherein the nickel-titanium alloy has a lower plateau stress of less than 250 M Pa.

14. The method of claim 11, wherein the nickel-titanium alloy has an elongation at fracture of greater than 15% in length.

15. The method of claim 11, further comprising forming the nickel-titanium alloy into an implantable medical device.

* * * * *